United States Patent
Rowe et al.

(10) Patent No.: US 7,806,928 B2
(45) Date of Patent: Oct. 5, 2010

(54) DIAGNOSTIC KIT TO ASSIST WITH HEART VALVE ANNULUS ADJUSTMENT

(75) Inventors: Stanton J. Rowe, Newport Beach, CA (US); Henry Bourang, Irvine, CA (US); Sepehr Fariabi, Newport Coast, CA (US); Jan Otto Solem, Stetten (CH)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 11/689,310

(22) Filed: Mar. 21, 2007

(65) Prior Publication Data
US 2007/0168023 A1    Jul. 19, 2007

Related U.S. Application Data

(62) Division of application No. 11/008,055, filed on Dec. 9, 2004, now Pat. No. 7,211,110.

(51) Int. Cl.
*A61F 2/24* (2006.01)
(52) U.S. Cl. .................. 623/2.37; 623/2.36; 600/508
(58) Field of Classification Search ............... 623/2.36, 623/2.37; 600/508
See application file for complete search history.

(56) References Cited

U.S. PATENT DOCUMENTS

| | | | |
|---|---|---|---|
| 4,164,046 A | 8/1979 | Cooley | |
| 4,655,771 A | 4/1987 | Wallsten | |
| 4,954,126 A | 9/1990 | Wallsten | |
| 5,006,106 A | 4/1991 | Angelchik | |
| 5,061,275 A | 10/1991 | Wallsten et al. | |
| 5,064,435 A | 11/1991 | Porter | |
| 5,071,407 A | 12/1991 | Termin et al. | |
| 5,104,404 A | 4/1992 | Wolff | |
| 5,163,955 A | 11/1992 | Love et al. | |
| 5,170,802 A | 12/1992 | Mehra | |
| 5,209,730 A | 5/1993 | Sullivan | |
| 5,224,491 A | 7/1993 | Mehra | |
| 5,304,131 A | 4/1994 | Paskar | |

(Continued)

FOREIGN PATENT DOCUMENTS

DE    196 05 042 A1    1/1998

(Continued)

OTHER PUBLICATIONS

Chinese Office Action dated May 22, 2009.

(Continued)

*Primary Examiner*—Carl H Layno
*Assistant Examiner*—Yun Haeng Lee
(74) *Attorney, Agent, or Firm*—Melinda R. Michalerya

(57) ABSTRACT

A diagnostic device for determining the amount of change required in a coronary sinus to reduce valve regurgitation. The device includes a distal tube having a distal anchor at a distal end portion of the distal tube, a proximal tube having a proximal anchor at a distal end portion of the proximal tube, and an adjustor to move the distal tube relative to the proximal tube. The proximal tube and the distal tube together form a telescoping elongate body adapted to fit within the coronary sinus, and the device includes a scale to measure the movement of the distal anchor relative to the proximal anchor.

8 Claims, 5 Drawing Sheets

U.S. PATENT DOCUMENTS

| | | | |
|---|---|---|---|
| 5,382,259 A | 1/1995 | Phelps et al. |
| 5,383,892 A | 1/1995 | Cardon et al. |
| 5,390,661 A | 2/1995 | Griffith et al. |
| 5,441,515 A | 8/1995 | Khosravi et al. |
| 5,449,373 A | 9/1995 | Pinchasik et al. |
| 5,476,471 A | 12/1995 | Shifrin et al. |
| 5,496,275 A | 3/1996 | Sirhan et al. |
| 5,531,779 A | 7/1996 | Dahl et al. |
| 5,534,007 A | 7/1996 | St. Germain et al. |
| 5,545,209 A | 8/1996 | Roberts et al. |
| 5,571,135 A | 11/1996 | Fraser et al. |
| 5,584,879 A | 12/1996 | Reimold et al. |
| 5,591,197 A | 1/1997 | Orth et al. |
| 5,593,442 A | 1/1997 | Klein |
| 5,607,444 A | 3/1997 | Lam |
| 5,674,280 A | 10/1997 | Davidson et al. |
| 5,713,949 A | 2/1998 | Jayaraman |
| 5,741,274 A | 4/1998 | Lenker et al. |
| 5,817,126 A | 10/1998 | Imran |
| 5,824,071 A | 10/1998 | Nelson et al. |
| 5,851,210 A | 12/1998 | Torossian |
| 5,876,419 A | 3/1999 | Carpenter et al. |
| 5,876,433 A | 3/1999 | Lunn |
| 5,891,108 A | 4/1999 | Leone et al. |
| 5,911,732 A | 6/1999 | Hojeibane |
| 5,919,233 A | 7/1999 | Knopf et al. |
| 5,935,081 A | 8/1999 | Kadhiresan |
| 5,954,761 A | 9/1999 | Machek et al. |
| 5,961,545 A | 10/1999 | Lentz et al. |
| 5,980,552 A | 11/1999 | Pinchasik et al. |
| 6,006,122 A | 12/1999 | Smits |
| 6,013,854 A | 1/2000 | Moriuchi |
| 6,019,739 A | 2/2000 | Rhee et al. |
| 6,027,525 A | 2/2000 | Suh et al. |
| 6,051,020 A | 4/2000 | Goicoechea et al. |
| 6,071,292 A | 6/2000 | Makower et al. |
| 6,077,296 A | 6/2000 | Shokoohi et al. |
| 6,093,203 A | 7/2000 | Uflacker |
| 6,110,100 A | 8/2000 | Talpade |
| 6,123,699 A | 9/2000 | Webster, Jr. |
| 6,161,029 A | 12/2000 | Spreigl et al. |
| 6,161,543 A | 12/2000 | Cox et al. |
| 6,165,169 A | 12/2000 | Panescu et al. |
| 6,168,619 B1 | 1/2001 | Dinh et al. |
| 6,171,329 B1 | 1/2001 | Shaw et al. |
| 6,183,411 B1 | 2/2001 | Mortier et al. |
| 6,203,556 B1 | 3/2001 | Evans et al. |
| 6,210,432 B1 | 4/2001 | Solem et al. |
| 6,221,103 B1 | 4/2001 | Melvin |
| 6,248,119 B1 | 6/2001 | Solem |
| 6,250,308 B1 * | 6/2001 | Cox ........................... 128/898 |
| 6,264,602 B1 | 7/2001 | Mortier et al. |
| 6,264,691 B1 | 7/2001 | Gabbay |
| 6,325,826 B1 | 12/2001 | Vardi et al. |
| 6,343,605 B1 | 2/2002 | Lafontaine |
| 6,350,277 B1 | 2/2002 | Kocur |
| 6,368,348 B1 | 4/2002 | Gabbay |
| 6,402,679 B1 | 6/2002 | Mortier et al. |
| 6,402,680 B2 | 6/2002 | Mortier et al. |
| 6,402,781 B1 | 6/2002 | Langberg et al. |
| 6,409,760 B1 | 6/2002 | Melvin |
| 6,537,314 B2 | 3/2003 | Langberg et al. |
| 6,569,198 B1 | 5/2003 | Wilson et al. |
| 6,626,899 B2 | 9/2003 | Houser et al. |
| 6,629,534 B1 | 10/2003 | St. Goar et al. |
| 6,656,221 B2 | 12/2003 | Taylor et al. |
| 6,669,687 B1 | 12/2003 | Saadat |
| 6,676,702 B2 | 1/2004 | Mathis |
| 6,706,065 B2 | 3/2004 | Langberg et al. |
| 6,709,456 B2 | 3/2004 | Langberg et al. |
| 6,764,510 B2 | 7/2004 | Vidlund et al. |
| 6,790,231 B2 | 9/2004 | Liddicoat et al. |
| 6,793,673 B2 | 9/2004 | Kowalsky et al. |
| 6,797,001 B2 | 9/2004 | Mathis et al. |
| 6,800,090 B2 | 10/2004 | Alferness et al. |
| 6,810,882 B2 | 11/2004 | Langberg et al. |
| 6,824,562 B2 | 11/2004 | Mathis et al. |
| 6,890,353 B2 | 5/2005 | Cohn et al. |
| 6,908,478 B2 | 6/2005 | Alferness et al. |
| 6,989,028 B2 | 1/2006 | Lashinski et al. |
| 6,997,951 B2 | 2/2006 | Solem et al. |
| 7,011,682 B2 | 3/2006 | Lashinski et al. |
| 7,044,967 B1 * | 5/2006 | Solem et al. ............... 623/2.36 |
| 7,090,695 B2 | 8/2006 | Solem et al. |
| 2001/0018611 A1 | 8/2001 | Solem et al. |
| 2001/0044568 A1 | 11/2001 | Langberg et al. |
| 2002/0016628 A1 | 2/2002 | Langberg et al. |
| 2002/0019660 A1 | 2/2002 | Gianotti et al. |
| 2002/0022880 A1 | 2/2002 | Melvin |
| 2002/0087173 A1 | 7/2002 | Alferness et al. |
| 2002/0103532 A1 * | 8/2002 | Langberg et al. ........... 623/2.36 |
| 2002/0103533 A1 | 8/2002 | Langberg et al. |
| 2002/0111533 A1 | 8/2002 | Melvin |
| 2002/0111647 A1 | 8/2002 | Khairkhahan et al. |
| 2002/0124857 A1 | 9/2002 | Schroeppel |
| 2002/0151961 A1 | 10/2002 | Lashinski et al. |
| 2002/0183837 A1 | 12/2002 | Streeter et al. |
| 2002/0183838 A1 | 12/2002 | Liddicoat et al. |
| 2002/0183841 A1 | 12/2002 | Cohn et al. |
| 2002/0188170 A1 | 12/2002 | Santamore et al. |
| 2003/0078465 A1 | 4/2003 | Pai et al. |
| 2003/0078654 A1 | 4/2003 | Taylor et al. |
| 2003/0083538 A1 | 5/2003 | Adams et al. |
| 2003/0105520 A1 * | 6/2003 | Alferness et al. ........... 623/2.36 |
| 2003/0120341 A1 | 6/2003 | Shennib et al. |
| 2003/0130730 A1 | 7/2003 | Cohn et al. |
| 2003/0135267 A1 | 7/2003 | Solem et al. |
| 2003/0144697 A1 | 7/2003 | Mathis et al. |
| 2003/0171806 A1 | 9/2003 | Mathis et al. |
| 2003/0204138 A1 | 10/2003 | Choi |
| 2003/0225454 A1 | 12/2003 | Mathis et al. |
| 2003/0236569 A1 | 12/2003 | Mathis et al. |
| 2004/0010305 A1 | 1/2004 | Alferness et al. |
| 2004/0019377 A1 | 1/2004 | Taylor et al. |
| 2004/0039443 A1 | 2/2004 | Solem et al. |
| 2004/0073302 A1 * | 4/2004 | Rourke et al. .............. 623/2.36 |
| 2004/0098116 A1 | 5/2004 | Callas et al. |
| 2004/0102839 A1 | 5/2004 | Cohn et al. |
| 2004/0102840 A1 | 5/2004 | Solem et al. |
| 2004/0102841 A1 | 5/2004 | Langberg et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0153147 A1 | 8/2004 | Mathis |
| 2004/0158321 A1 * | 8/2004 | Reuter et al. ............... 623/2.36 |
| 2004/0176840 A1 | 9/2004 | Langberg et al. |
| 2004/0186566 A1 | 9/2004 | Hindrichs et al. |
| 2004/0210240 A1 | 10/2004 | Saint |
| 2004/0220654 A1 | 11/2004 | Mathis et al. |
| 2004/0220657 A1 | 11/2004 | Nieminen et al. |
| 2004/0254600 A1 | 12/2004 | Zarbatany et al. |
| 2004/0267358 A1 | 12/2004 | Reitan |
| 2005/0004667 A1 | 1/2005 | Swinford et al. |
| 2005/0010240 A1 | 1/2005 | Mathis et al. |
| 2005/0021121 A1 | 1/2005 | Reuter et al. |
| 2005/0027351 A1 | 2/2005 | Reuter et al. |
| 2005/0043792 A1 | 2/2005 | Solem et al. |
| 2005/0060030 A1 | 3/2005 | Lashinski et al. |
| 2005/0080483 A1 | 4/2005 | Solem et al. |
| 2005/0096740 A1 | 5/2005 | Langberg et al. |
| 2005/0177228 A1 | 8/2005 | Solem et al. |

| | | | |
|---|---|---|---|
| 2005/0222678 A1 | 10/2005 | Lashinski et al. | |
| 2006/0116756 A1 | 6/2006 | Solem et al. | |
| 2006/0116757 A1 | 6/2006 | Lashinski et al. | |
| 2006/0184230 A1 | 8/2006 | Solem et al. | |

FOREIGN PATENT DOCUMENTS

| | | |
|---|---|---|
| DE | 196 11 755 A1 | 2/1998 |
| EP | 0 727 239 A2 | 8/1996 |
| WO | WO 95/16407 | 6/1995 |
| WO | WO 96/34211 | 10/1996 |
| WO | WO96/34211 | 10/1996 |
| WO | WO 96/40356 | 12/1996 |
| WO | WO 98/18411 | 5/1998 |
| WO | 98/51365 A1 | 11/1998 |
| WO | WO 99/44534 | 9/1999 |
| WO | WO 99/53977 | 10/1999 |
| WO | WO 00/18320 | 4/2000 |
| WO | WO 00/41649 | 7/2000 |
| WO | WO 00/44313 A1 | 8/2000 |
| WO | WO00/74565 | 12/2000 |
| WO | WO 01/00111 A1 | 1/2001 |
| WO | WO 01/50985 A1 | 7/2001 |
| WO | WO 01/54618 A1 | 8/2001 |
| WO | WO 01/85061 A2 | 11/2001 |
| WO | WO 01/89426 A1 | 11/2001 |
| WO | WO 02/00099 A2 | 1/2002 |
| WO | WO 02/01999 A2 | 1/2002 |
| WO | WO 02/05888 A1 | 1/2002 |
| WO | WO 02/34118 A2 | 5/2002 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 02/076284 A2 | 10/2002 |
| WO | WO 02/078576 A2 | 10/2002 |
| WO | WO 02/096275 A2 | 12/2002 |
| WO | WO03/037171 | 5/2003 |
| WO | WO 03/037171 A2 | 5/2003 |
| WO | WO 2004/019816 A2 | 3/2004 |
| WO | WO 2004/045463 A2 | 6/2004 |
| WO | WO 2004/084746 A2 | 10/2004 |

OTHER PUBLICATIONS

Laaksovirta et al., *Expansion and bioabsorption of the self-reinforced lactic and glycolic acid copolymer prostatic spiral stent*, PubMed, Excerpt from J Urol 2001 Sep.; 166(3):919-22, one sheet.

Liu et al., *Sutural expansion osteogenesis for management of the bony-tissue defect in cleft palate repair: experimental studies in dogs*, PubMed, Excerpt from Plast Reconstr Surg May 2000; 105(6):2012-25; discussion 2026-7, two sheets.

Yoneyama et al., *Super-elastic property of Ti-Ni alloy for use in dentistry*, PubMed, Excerpt from Front Med Biol Eng 2000; 10(2):97-103, one sheet.

Kotian, *Shape memory effect and super elasticity it's dental applications*, PubMed, Excerpt from Indian J Dent Res Apr.-Jun. 2001; 12(2):101-4, one sheet.

Kuo et al., *The use of nickel-titanium alloy in orthopedic surgery in China*, PubMed, Excerpt from Orthopedics Jan. 1989; 12(1):111-6, one sheet.

Civjan et al., *Potential applications of certain nickel-titanium (nitinol) alloys*, PubMed, Excerpt from J Dent Res Jan.-Feb. 1975;54(1):89-96, one sheet.

Brennan, *Suite of Shape-Memory Polymers*, http:///pubs.acs.org/cen/topstory/7906notw1.html, News of the Week Materials, Feb. 5, 2001, vol. 79, No. 6, Cenear 79 6 pp. 5, ISSN 0009-2347, three sheets.

Stikeman, *Total Recall*, An MIT Enterprise Technology Review - Innovation, Jun. 2001, two sheets.

European Patent Office Office action dated Dec. 22, 2003 for Application No. 00 946 661.6 -2310, 4 sheets.

Written Opinion dated Nov. 8, 2002 for International application No. PCT/EP01/10371, 14 sheets.

International Search Report dated Apr. 23, 2002 for International application No. PCT/EP 01/10371, 4 sheets.

International Search Report dated Mar. 15, 2000 for National application No. SE 9902455-6, 3 sheets.

International Search Report dated Oct. 9, 2002 for National application No. SE 0200073-5, 5 sheets.

International Search Report dated Jun. 5, 2003 for International application No. PCT/EP 02/14655, 7 sheets.

Buchanan et al., Circumferential Suture of the Mitral Annulus for Correction of Mitral Regurgitation in Dogs, Veterinary Surgery, 27: 182-193, 1998.

Buchanan JW, Sammarco CD, Circumferential Suture of the Mitral Annulus for Correction of Mitral Regurgitation in Dogs, PubMed, Excerpt from Vet Surg May-Jun. 1998;27(3):183-93, abstract, one sheet.

International Search Report for PCT/US2005/044373.

\* cited by examiner

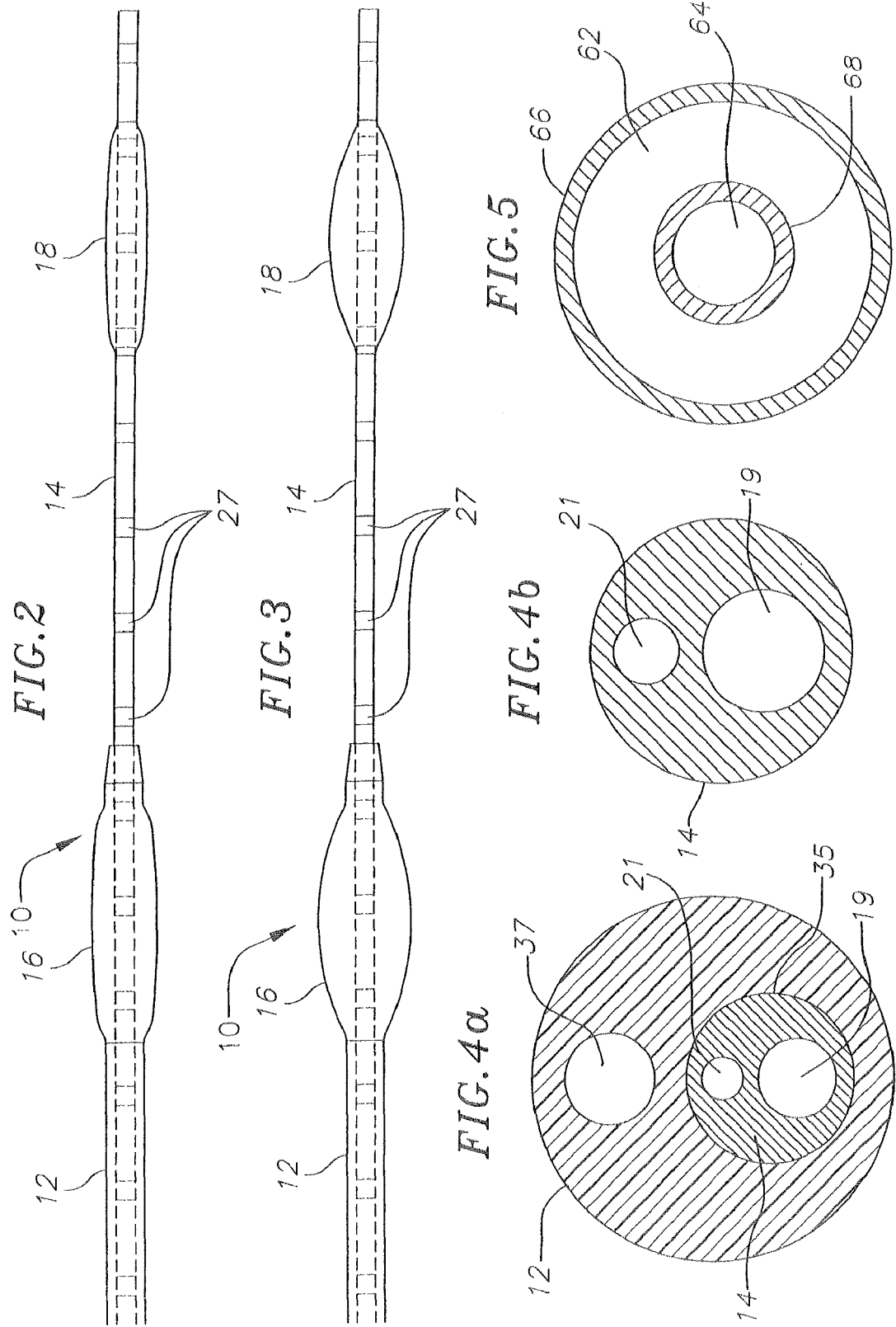

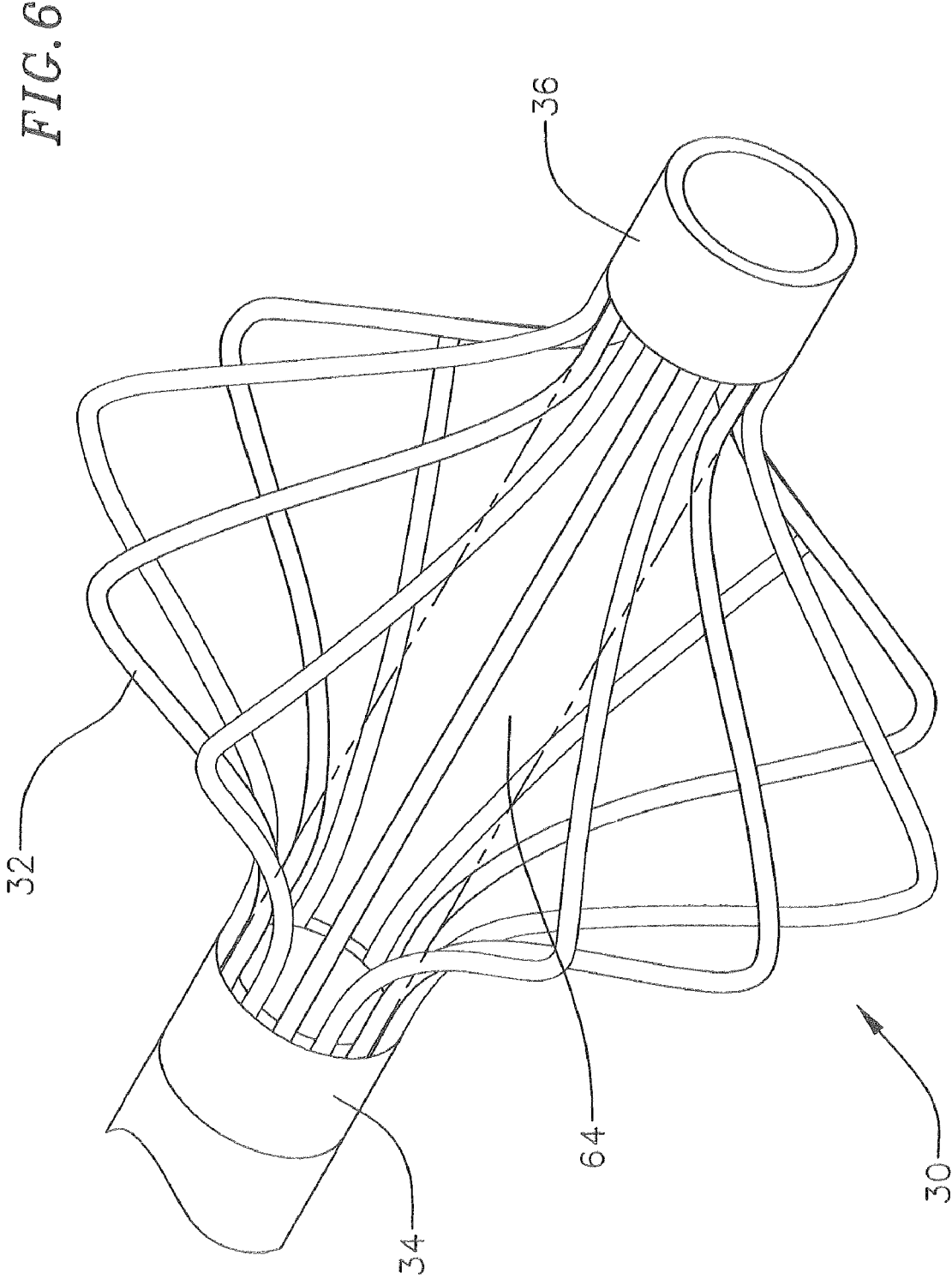

DIAGNOSTIC KIT TO ASSIST WITH HEART VALVE ANNULUS ADJUSTMENT

CROSS-REFERENCE TO RELATED APPLICATIONS

This application is a divisional of U.S. patent application Ser. No. 11/008,055, now U.S. Pat. No. 7,211,110, filed Dec. 9, 2004, which is incorporated herein by reference in its entirety.

FIELD OF THE INVENTION

This invention relates to apparatus and methods for heart valve repair and, more particularly, to a diagnostic kit to assist with heart valve annulus adjustment for improving heart valve function using devices inserted into vessels surrounding the target valve.

BACKGROUND

Heart valve regurgitation, or leakage from the outflow to the inflow side of a heart valve, is a common occurrence in patients with heart failure and a source of morbidity and mortality in these patients. Usually regurgitation will occur in the mitral valve, located between the left atrium and left ventricle, or in the tricuspid valve, located between the right atrium and right ventricle. Mitral regurgitation in patients with heart failure is caused by changes in the geometric configurations of the left ventricle, papillary muscles and mitral annulus. Similarly, tricuspid regurgitation is caused by changes in the geometric configurations of the right ventricle, papillary muscles and tricuspid annulus. These geometric alterations result in mitral and tricuspid leaflet tethering and incomplete coaptation in systole.

Heart valve repair is the procedure of choice to correct heart regurgitation of all etiologies. With the use of current surgical techniques, between 40% and 60% of regurgitant heart valves can be repaired, depending on the surgeon's experience and the anatomic conditions. The advantages of heart valve repair over heart valve replacement are well documented. These advantages include better preservation of cardiac function and reduced risk of anticoagulant-related hemorrhage, thromboembolism and endocarditis.

Recently, several developments in minimally invasive techniques for repairing heart valves without surgery have been introduced. Some of these techniques involve introducing systems for remodeling the mitral annulus through the coronary sinus.

The coronary sinus is a blood vessel commencing at the coronary ostium in the right atrium and passing through the atrioventricular groove in close proximity to the posterior, lateral and medial aspects of the mitral annulus. Because of its position adjacent to the mitral annulus, the coronary sinus provides an ideal conduit for positioning an endovascular prosthesis to act on the mitral annulus and thereby reshape it.

Examples of minimally invasive apparatus for heart valve repair can be found in U.S. Pat. No. 6,210,432 to Solem, et al., U.S. Pat. No. 7,192,442 to Solem, et. al., U.S. Pat. No. 7,090,695 to Solem, et. al., U.S. Pat. No. 7,192,443 to Solem, et. al., U.S. Pat. No. 6,997,951 to Solem, et. al., U.S. Ser. No. 10/714,462 to Solem, et. al. filed on Nov. 13, 2003 and U.S. Ser. No. 60/530,352 to Solem, et al. filed on Dec. 16, 2003 (the '352 application) all of which are incorporated herein by reference.

One specific example of a minimally invasive apparatus for heart valve repair, as described in greater detail in the '352 application, and as shown in FIGS. 10 and 11 herein, includes an elongate body 410 having a proximal anchor 412 and a distal anchor 414 connected by a bridge 416. The proximal and distal anchors 412, 414 are both stents made from nitinol and both anchors have a mesh configuration including loops 54 of zigzag shaped material having alternating peaks 42. The loops 54 are connected at each peak 42 to form rings 56 of four-sided openings. Both the proximal anchor 412 and the distal anchor 414 are transferable between a compressed state, in which the anchors have a diameter that is less than the diameter of the coronary sinus, and an expanded state, in which the anchors have a diameter that is about equal to or greater than the diameter of the coronary sinus.

As shown in FIG. 10, the bridge 416 is connected between the proximal anchor 412 and the distal anchor 414 by links 418, 419. As shown in more detail in FIG. 11, the link 419 has a base 421 and arms 422 that extend from the base and which are connected to the anchor 414. The link also includes a hole 428 which serves as a means through which resorbable thread 420 may be secured to the bridge.

The bridge 416 is made from a shape memory material and is flexible to allow the body 410 to conform to the shape of the coronary sinus. The bridge 416 includes connected X-shaped elements 424 having a space 425 between adjacent elements. The bridge has two states, an activated state in which the bridge 416 has a first length and a non-activated state, in which the bridge has a second length, the second length being longer than the first length. Resorbable thread 420 which acts as a temporary spacer is woven into the spaces 425 to hold the bridge in its longer non-activated state.

The body is inserted into the coronary sinus of a patient with both anchors 412, 414, in the compressed state and the bridge 416 including resorbable thread 420 in the longer non-activated state. After the anchors 412, 414 are placed in a desired location, they are transformed into their expanded state in which they serve to attach the body 410 to the coronary sinus. After a period of time, during which the wall of the coronary sinus grows around the anchors 412, 414, the resorbable thread dissolves and the bridge 416 transforms from its longer non-activated state to its shorter activated state. The shortening of the bridge 416 draws the proximal anchor 412 and the distal anchor 414 closer together, cinching the coronary sinus and reducing its circumference. This reduction of the circumference of the coronary sinus closes the gap causing mitral regurgitation.

Valve annulus reshaping devices, including those described above, may be manufactured such that they can vary in certain dimensions or characteristics. For instance, the devices may be manufactured so that they foreshorten or otherwise change shape by a specific amount depending on how much reshaping of a valve is necessary. In other words, a physician may have a choice between using a reshaping device that severely remodels an annulus, one that only slightly remodels an annulus, or one that is custom designed to remodel an annulus by a specific amount. Additionally, the valve reshaping devices may also be manufactured to have different lengths and/or anchor sizes. Due to varying degrees of the severity of mitral and tricuspid valve leaflet coaptation as well as varying sizes and lengths of heart valve annuli, it would be advantageous for a physician to know how much reshaping of the valve annulus is necessary as well as having an idea of the size and length of the annulus before inserting the valve reshaping device. This knowledge would allow the physician to choose a device that could reshape the valve annulus by an appropriate amount. Thus, there is a need for a device that a physician may use to gauge the amount of reshaping necessary in a heart valve annulus and/or the size and length of the annulus. Such a device would allow the physician to select an annulus reshaping device to insert into a patient that more closely approximates the amount of reshaping necessary for that specific patient as well as a device that may be custom designed to fit the size and length of the patient's annulus.

SUMMARY

A diagnostic device for determining the amount of change desired in a cardiac vessel to reduce valve regurgitation is disclosed. The diagnostic device comprises a distal tube (or other suitable elongate body) having a distal anchor attached at a distal end of the distal tube, a proximal tube (or other suitable elongate body) having a proximal anchor attached at a distal end of the proximal tube, and an adjustor by which the distal tube may be moved relative to the proximal tube. In one embodiment, the device may be inserted into the coronary sinus. The proximal tube and the distal tube together form a telescoping elongate body adapted to fit within the coronary sinus. Additionally, the distal tube includes a plurality of radiopaque markers spaced evenly thereon to provide a means for measuring the distance moved by the distal tube relative to the proximal tube, the distal anchor and the proximal anchor are transformable between a compressed state and an expanded state, and movement of the adjustor by a specified distance causes movement of the distal tube by the same distance. The proximal and distal anchors may be balloons, baskets or stents.

A method for determining the amount of change to the coronary sinus necessary to reduce mitral regurgitation is also disclosed. Such method includes inserting a diagnostic device into the coronary sinus, anchoring a distal anchor to the coronary sinus, anchoring a proximal anchor to the coronary sinus, using an adjustor to move the distal anchor proximally such that mitral regurgitation is reduced and measuring the proximal movement of the distal anchor and simultaneously measuring the amount of mitral valve regurgitation.

BRIEF DESCRIPTION OF THE DRAWINGS

FIG. 2 is a side view of one exemplary embodiment of a diagnostic device of the present invention including a proximal tube with a proximal anchor and a distal tube with a distal anchor in a compressed state.

FIG. 3 is a side view of embodiment of FIG. 2 including a proximal anchor and a distal anchor in an expanded state.

FIG. 4a is a cross-sectional view of a telescoped proximal tube and distal tube of the current invention.

FIG. 4b is a cross-sectional view of a distal tube of the current invention.

FIG. 5 is a cross-sectional view of a coaxial proximal tube and distal tube of the current invention.

FIG. 6 is a perspective view of an alternate anchor according to the present invention.

DETAILED DESCRIPTION

Although the devices and methods described below may be used in any appropriate heart valve annulus, for ease and consistency of explanation the devices and methods below will be described with specific reference to the mitral valve and mitral annulus.

Figure 1:
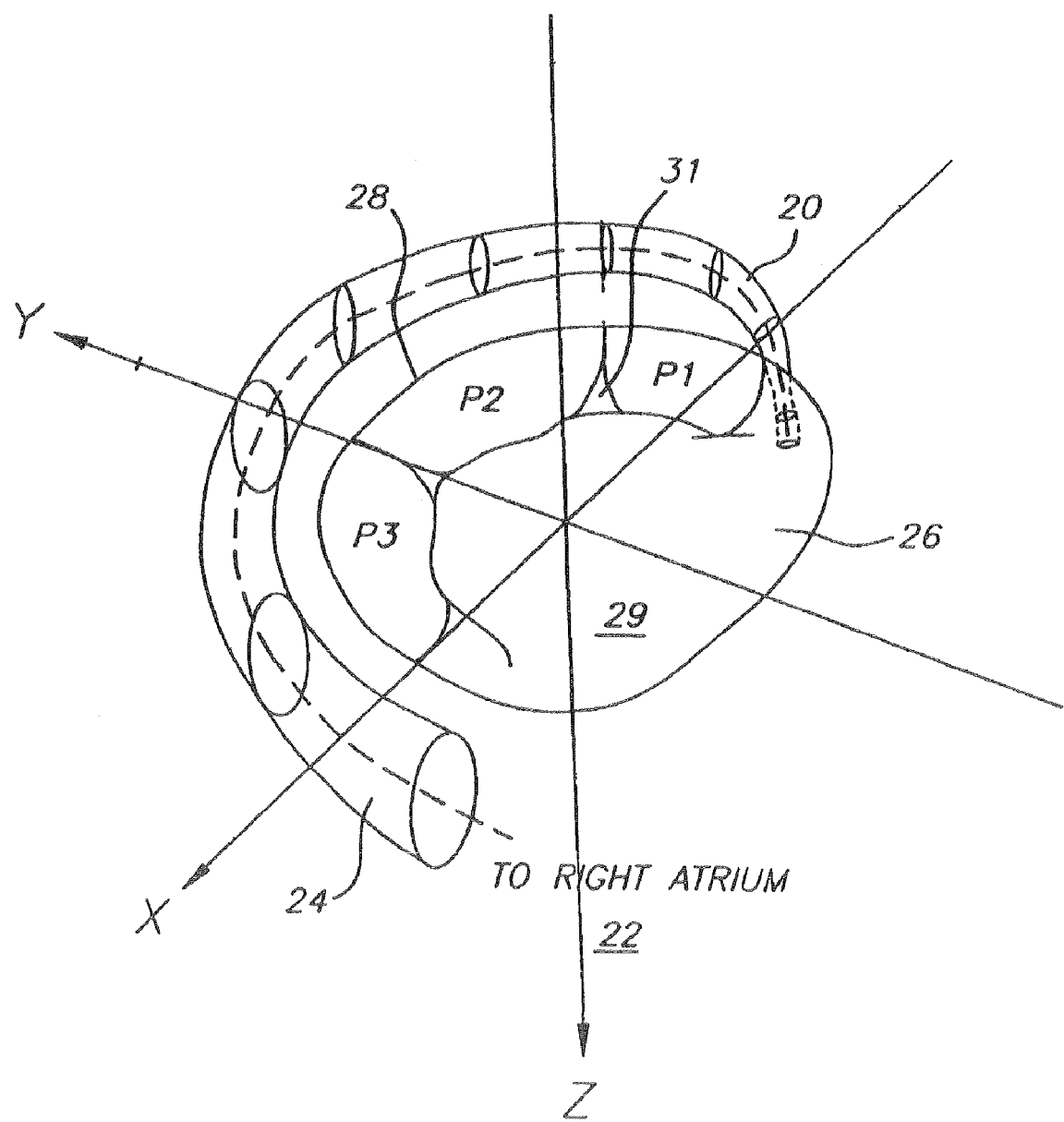
FIG. 1 is a three-dimensional view of the mitral valve and coronary sinus.

Referring to FIG. 1, a coronary sinus 20 extends from a right atrium 22 and a coronary ostium 24 and wraps around a mitral valve 26. The term coronary sinus is used herein as a generic term to describe a portion of the vena return system that is situated adjacent to the mitral valve 26 along the atrioventricular groove. The term coronary sinus 20 used herein generally includes the coronary sinus, the great cardiac vein and the anterior interventricular vein. A mitral annulus 28 is a portion of tissue surrounding a mitral valve orifice to which several leaflets attach. The mitral valve 26 has two leaflets, an anterior leaflet 29 and a posterior leaflet 31. The posterior leaflet has three scallops P1, P2 and P3 which, in a healthy mitral valve coapt with the anterior leaflet 29 to prevent regurgitation of blood through the valve.

The problem of mitral regurgitation often results when a posterior aspect of the mitral annulus 28 dilates and displaces one or more of the posterior leaflet scallops P1, P2 or P3 away from the anterior leaflet 29 causing a gap to be formed through which regurgitation occurs. To reduce or eliminate mitral regurgitation, therefore, it is desirable to move the posterior aspect of the mitral annulus 28 in an anterior direction and close the gap caused by the leaflet displacement.

As shown in FIGS. 2 and 3, an embodiment of the diagnostic device 10 of the present invention comprises a proximal tube 12 and a distal tube 14. The diagnostic device 10 may be of dimensions such that it is insertable into a vessel adjacent a heart valve such as the coronary sinus and the anterior right ventricular cardiac vein. Additionally, the diagnostic device 10 may be flexible enough to allow it to adapt to the curvature of the vessel into which it is inserted.

As shown in FIG. 4a, the proximal tube 12 may be a plastic tube having two lumens, a tube lumen 35 and an inflation lumen 37. The tube lumen 35 allows the distal tube 14 to pass through the proximal tube 12. The inflation lumen serves as a channel through or by which an inflation gas or liquid may expand an anchor, as is also described in greater detail below. This tube configuration may be used when the anchor is inflatable, such as a balloon.

As shown in FIG. 4b, the distal tube may also contain two lumens, a guidewire lumen 19 and an inflation lumen 21. The guidewire lumen 19 serves as a channel on which the distal tube 14 may travel as it is inserted into a patient as is described in greater detail below. The inflation lumen 21 serves as a channel through or by which an inflation gas or liquid may expand an anchor, as is also described in greater detail below. This tube configuration may be used when the anchor is inflatable, such as a balloon.

FIG. 5 shows an alternate configuration wherein the distal tube 14 includes an inner tube 68 and an outer tube 66 that are coaxial. Based on this configuration, a guidewire lumen 64 is formed inside the inner tube 68 and an expansion lumen 62 is formed between the inner tube and the outer tube 66. This tube configuration may be used when the anchor is inflatable, such as a balloon, or mechanically expandable, such as a basket. This coaxial tube configuration may also be used for the proximal tube 12. It will also be appreciated that in some configurations the proximal tube 12 passes through the distal tube, rather than vice versa, as described above.

The distal tube 14 may further include radiopaque marker bands 27 spaced along the outer perimeter of the tube as shown in FIG. 2. The marker bands 27, which are visible under fluoroscopy, serve to indicate the position of the distal tube 14 when the tube is positioned within a vessel. Additionally, the marker bands 27 may be used to measure a desired portion of the coronary sinus and the amount of movement by the distal tube 14 as is described in greater detail below. The marker bands 27 may be platinum bands or any other biocompatible band visible under fluoroscopy or other suitable visual means. The specific number of bands 27 included along the distal tube 14 is not critical, but preferably there are a sufficient number of bands to allow the entire exposed length of the tube in the coronary sinus to be visible under fluoroscopy. Further, there are a sufficient number of bands 27 to allow the bands to act as distance markers for movement of the distal tube 14. A similar number of markers are located on the distal tube outside of the patient visible for the human eye. These markers are visible and may be counted even without the help of fluoroscopy.

The distal tube 14 also includes a distal anchor 18 located at or near the distal end of the distal tube. In one embodiment, the distal anchor 18 has two states, a compressed state and an expanded state. In the compressed state, the distal anchor 18 is insertable into the coronary sinus 20 or other coronary vessel. In the expanded state, the distal anchor 18 secures the distal tube 14 to an inner wall of the vessel into which it has been inserted. The distal anchor 18 is transformable from the compressed state to the expanded state by a transformation means. Such transformation means may be mechanical, electrical or chemical. Additionally, the distal anchor 18 may be self-expanding.

As shown in FIGS. 2 and 3 in one exemplary embodiment, the distal anchor 18 is a compliant balloon which conforms to the size and shape of the vessel into which it is expanded. The balloon may be attached to the distal or proximal tube by a thermal or adhesion bond, or by any other appropriate attachment means. The balloon may be manufactured such that it has a safety mechanism that will reduce the possibility of the balloon damaging a vessel into which it is inserted. For instance, the balloon may be designed to have a maximum pressure to which it can be inflated. Additionally, the balloon may be designed with a "slow leak" which gradually reduces its internal pressure. Since the compliant balloon will conform to the size of the vessel and because the balloon is visible under fluoroscopy, an observer will be able determine the size of the vessel at the balloon location by viewing the balloon on a screen having dimension markers. Knowing the approximate size of the vessel into which a valve repair device will be inserted may allow for a more accurate decision to be made as to which particular valve repair device should be selected from an array of devices to use on a patient. In alternate embodiments of the diagnostic device 10, the distal anchor 18 may be a basket, a stent, or any other expandable device adapted to secure the device inside a vessel.

The balloon may be transformed from its compressed state to its expanded state by using a biocompatible fluid, and more specifically, a saline solution. The fluid may be introduced through a catheter (not shown) and may be transported through the inflation lumen 21, 62 (FIGS. 4 and 5) to the balloon.

In an alternate embodiment as shown in FIG. 6, a basket 30 may be used as a distal anchor. In one embodiment, the basket 30 has two states, a compressed state and an expanded state. In the compressed state, the basket 30 is insertable into the coronary sinus or other coronary vessel. More specifically, in the compressed state the basket 30 may be substantially cylindrical and may include a plurality of strands 32 extending longitudinally from a proximal end 34 to a distal end 36 of the basket spaced evenly around the basket's circumference. The distal end 36 of the basket 30 may be adapted to be fitted onto an inner tube 68 and the proximal end 34 of the basket may be adapted to be fitted onto an outer tube 66 (see FIG. 5). In one embodiment, the outer tube 66 may also be the distal tube 14. When the inner tube 68 and the outer tube 66 are moved relative to each other, the basket 30 may be expanded or contracted. In the expanded state, the basket 30 is secured to an inner wall of the vessel into which it has been inserted. In the expanded state, wherein the distance between the proximal end 34 and the distal end 36 of the basket 30 is decreased, the strands 32 may become triangularly-shaped with the apex of the triangle protruding away from the center of the basket. In one exemplary embodiment, the strands 32 may be made from a shape memory material (e.g. nitinol) allowing the basket 30 to transform from its compressed state to its expanded state by, for example, retraction of a sheath (not shown) covering the basket.

Similarly to the distal tube 14, the proximal tube 12 may have a proximal anchor 16 located at or near the distal end of the proximal tube. Like the distal anchor 18, the proximal anchor 16 may have a compressed state for delivery into a vessel and an expanded state for anchoring the distal tube to the vessel. The proximal tube 12 may further include an inflation lumen 37 for transforming the proximal anchor 16 between the compressed state and the expanded state.

The distal tube 14 and the proximal tube 12 of the diagnostic device 10 may be slidably connected to each other in a telescoping manner to form an elongate body. In one exemplary embodiment, the outer diameter of the proximal tube 12 is greater than the outer diameter of the distal tube 14, allowing the distal tube to fit within the proximal tube. The movement of the distal tube 14 may be controlled by using a handle (not shown). More specifically, the distal tube 14 may be attached to a collar which is slidable along the handle. When the collar is moved proximally, the distal tube 14 is also moved proximally by the same distance. Similarly, when the collar is moved distally, the distal tube 14 is moved distally by the same distance. In one exemplary embodiment, the body of the handle may include distance markers which allow the movement of the collar, and thus the movement of the distal tube 14, to be measured.

In one exemplary embodiment, the diagnostic device 10 may be deployed as follows. First, a guidewire (not shown) is inserted into the coronary sinus past the great cardiac vein and deep into the arterioventricular vein. The diagnostic device 10 may be mounted coaxially on a delivery catheter (not shown), and inserted into the coronary sinus 20 over the guidewire. Proximal ends of the distal tube 14 and proximal tube 12 may extend out of the patient's body where they are attached to a handle. Additionally, the proximal anchor 16 and the distal anchor 18 are adjacent as the diagnostic device 10 is inserted into the coronary sinus 20.

Figure 7:
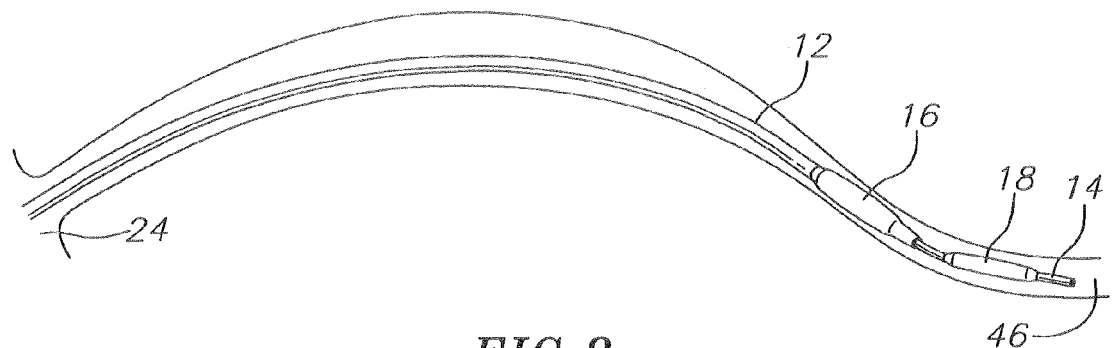
FIG. 7 is a side view of the diagnostic device of FIG. 2 after the device has been initially inserted into the coronary sinus and before expansion of the distal anchor.

When initially inserted into a patient, the diagnostic device 10 is inserted into the coronary sinus 20 as distally as possible. Specifically, the diagnostic device 10 may be inserted into the part of the coronary sinus known as the great cardiac vein 46 as shown in FIG. 7. Because of its naturally curved shape and higher concentration of fatty tissue, the great cardiac vein 46 allows for high resistance to movement and provides a natural anchoring location for the distal anchor 18.

Once the distal tube 14, and more specifically, the distal anchor 18 have been placed in the desired position in the coronary sinus 20, the distal anchor may be transformed from its compressed state into its expanded state in one embodiment, where the distal anchor 18 is a balloon, a biocompatible fluid will be introduced into the inflation lumen 37 to inflate the balloon. In an alternate embodiment, where the distal anchor 18 is a mechanically expandable anchor, such as a basket 30 (FIG. 6), manipulation of the inner tube 68 and the outer tube 66 (FIG. 5) will cause the anchor to transform into its expanded state. In yet another embodiment, where the anchor is self-expandable, a delivery sheath is used to cover the anchors and retraction of the delivery sheath will cause the anchor to transform into its expanded state.

Figure 8:
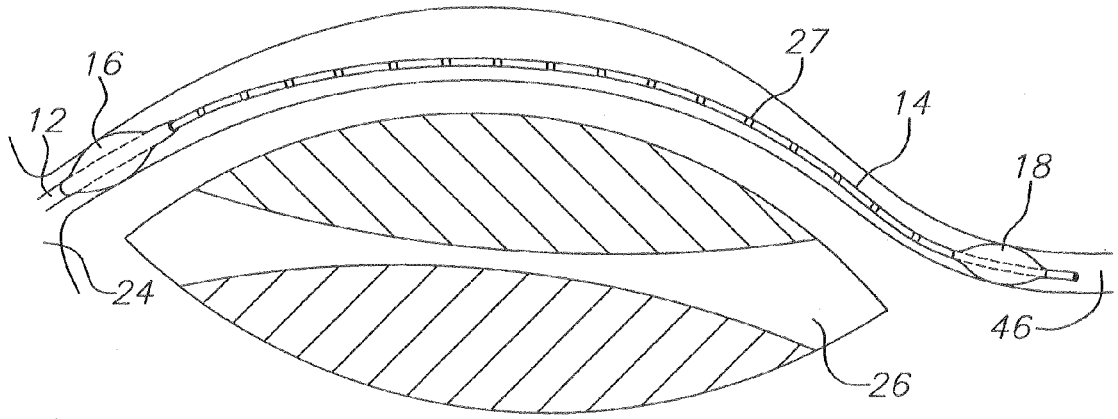
FIG. 8 is a side view of the diagnostic device of FIG. 2 positioned for use in the coronary sinus with the distal anchor and the proximal anchor in the expanded state.

Once the distal anchor 18 has been expanded such that the anchor is in contact with the inner walls of the coronary sinus 20, the proximal tube 12 is pulled proximally using the handle. The distance markers on the handle as well as the radiopaque markers 27 on the distal tube 14 allow the distance that the proximal tube 12 has moved to be measured. The proximal tube 12 is pulled proximally until the proximal anchor 16 is adjacent the ostium 24 of the coronary sinus 20. Alternatively, the proximal anchor may be placed in the right atrium outside of the coronary sinus ostium 24, abutting the ostium, but not blocking the ostium. Radiopaque markers 27 on the distal tube 14 are visible on a monitoring screen and aid a user in locating the proximal anchor 16 in the coronary sinus 20. After the proximal anchor 16 is placed in its desired location, the proximal anchor is transformed from its compressed state into its expanded state (FIG. 8). As described above, in an embodiment wherein the proximal anchor 16 is a balloon, a biocompatible fluid will be introduced into the inflation lumen 21 to inflate the balloon In the embodiment wherein the proximal anchor 16 is a self-expanding anchor, such as a basket 30 (FIG. 6), the retraction of the delivery sheath proximal to the proximal anchor will cause the anchor to transform into its expanded state.

Figure 9:
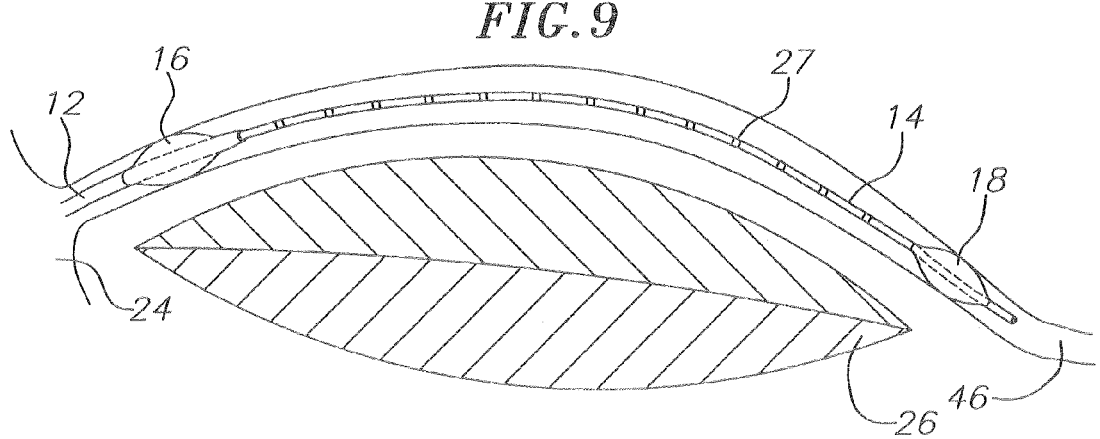
FIG. 9 is a side view of the diagnostic device of FIG. 2 after the device has been used to reduce an anterior-posterior distance between leaflets of a mitral valve.
Figure 10:
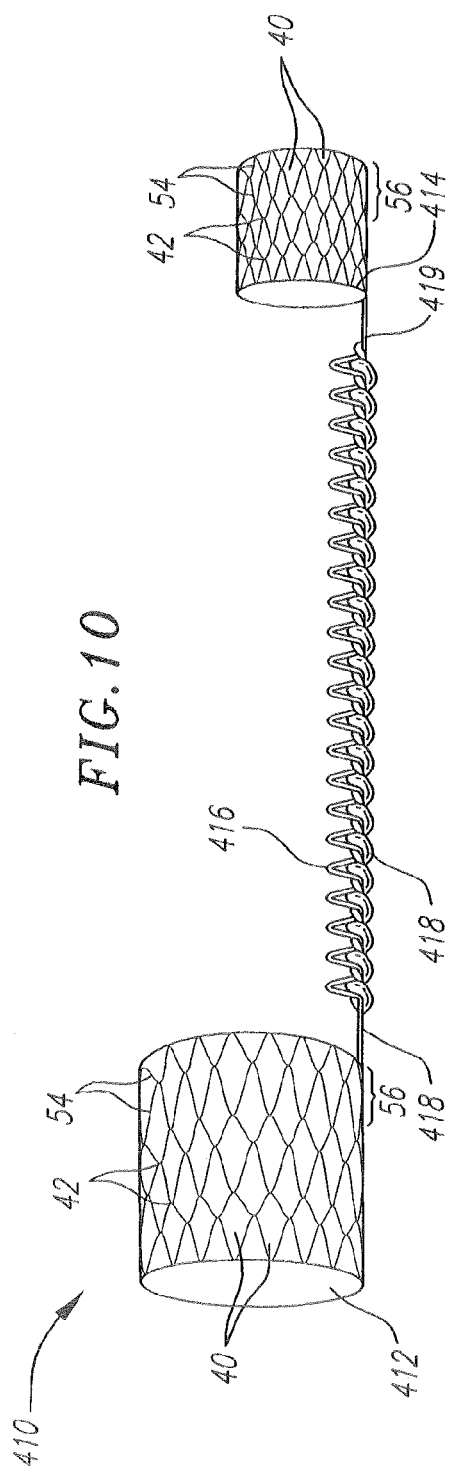
FIG. 10 is an exemplary embodiment of a recent mitral valve repair device.
Figure 11:
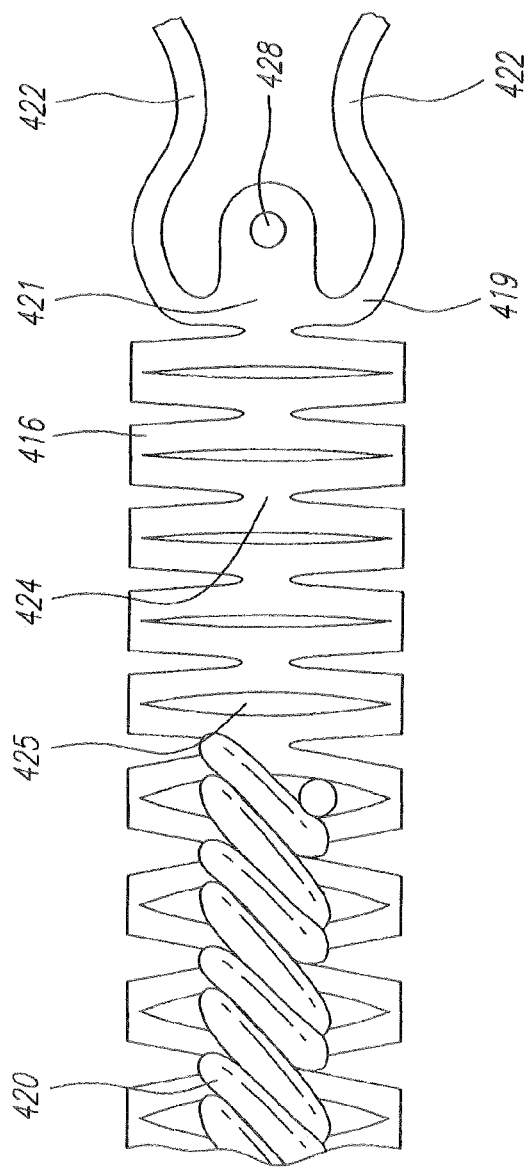
FIG. 11 is a detail of the mitral valve repair device of FIG. 10.

Once both the proximal anchor 16 and the distal anchor 18 have been transformed from their compressed state into their expanded state, the handle may be used to pull the distal tube 14 proximally. Pulling the distal tube 14 proximally will have at least one of two effects on the coronary sinus 20. The first effect may be to cinch the coronary sinus 20 tighter around the mitral valve 26, decreasing the distance between the anterior leaflet 29 and posterior leaflets 31. The second effect may be to decrease the radius of curvature of the coronary sinus 20, which may also decrease the distance between the anterior leaflet 29 and posterior leaflets 31. This change in the shape of the mitral valve 26 allows the gap caused by mitral regurgitation between the anterior leaflet 29 and the posterior leaflet 31 to close (FIG. 9), thus decreasing or eliminating mitral regurgitation.

As the radius of curvature of the coronary sinus is decreased and the gap between the anterior leaflet 29 and posterior leaflet 31 of the mitral valve is reduced, the amount of regurgitation is measured. This measurement is preferably performed by ultrasound with the ultrasound probe located on the chest, in the esophagus or inside the heart of the patient. When the regurgitation is at a minimum, and particularly when there is no regurgitation, the distance the distal tube 14 has moved relative to the proximal tube is noted, for instance, by using the radiopaque markers as a measuring tool.

Once mitral regurgitation has been eliminated or reduced by the desired amount, and the distance the distal tube 14 must be moved to achieve the desired effect has been measured, the distal anchor 18 and the proximal anchor 16 are transformed back from their expanded state to their compressed state. In the embodiment where the anchors 16, 18 are balloons, the fluid used to inflate the balloons is removed. In the embodiment where the anchors 16, 18 are self-expanding, the delivery sheath is reinserted over each anchor. In the embodiment where the anchors 16, 18 are baskets 30, the inner tube 68 and the outer tube 66 are moved apart from one another to transform the anchor into its compressed state.

After the proximal anchor 16 and the distal anchor 18 have been returned to their compressed state, the proximal tube 12 and the distal tube 14 are retracted proximally along the guidewire from the coronary sinus 20 and out of the patient's body. Once the diagnostic device 10 has been removed, a valve repair device may be inserted along the guidewire to more permanently repair the mitral valve regurgitation. Based on information about the coronary sinus 20 received from the diagnostic device 10, such as the length of the coronary sinus, and information about the amount of foreshortening necessary to achieve the desired reduction of mitral regurgitation, an appropriate valve repair device may be selected from an array of such devices having various (or variable) diameters and/or foreshortening lengths.

While the foregoing described the preferred embodiments of the invention, it will be obvious to one skilled in the art that various alternatives, modifications and equivalents may be practiced within the scope of the appended claims.

What is claimed is:

1. A diagnostic device for determining an amount of adjustment required in a coronary sinus to reduce heart valve regurgitation comprising:
    a first elongate body having a distal anchor at a distal end portion of the first elongate body,
    a second elongate body having a proximal anchor at a distal end portion of the second elongate body, and
    an adjustor to move one of the first and second elongate body relative to the other of the first and second elongate bodies,
    wherein the first and second elongate bodies together form a telescoping elongate body adapted to fit within the coronary sinus, and
    further comprising a scale to permit measurement of the movement of the distal anchor relative to the proximal anchor, wherein the scale is on the adjustor.

2. The diagnostic device of claim 1, wherein the distal anchor and the proximal anchor are transformable between a compressed state and an expanded state.

3. The diagnostic device of claim 1, wherein movement of the adjustor by a certain distance causes movement of the first elongate body by the same distance.

4. The diagnostic device of claim 1, wherein the distal anchor and the proximal anchor comprise balloons.

5. The diagnostic device of claim 4, wherein the distal anchor and the proximal anchor are transformed from their compressed state to their expanded state by a fluid.

6. The diagnostic device of claim 1, wherein the distal anchor comprises a basket.

7. The diagnostic device of claim 1, wherein each of the first and second elongated bodies contain an inflation lumen and a guidewire lumen.

8. The diagnostic device of claim 1, wherein the adjustor comprises a handle.

* * * * *